United States Patent
King et al.

(10) Patent No.: US 7,781,526 B2
(45) Date of Patent: Aug. 24, 2010

(54) MEDICAL IMPLANT OR MEDICAL IMPLANT PART COMPRISING POROUS UHMWPE AND PROCESS FOR PRODUCING THE SAME

(75) Inventors: Richard S. King, Warsaw, IN (US); Mark D. Hanes, Winona Lake, IN (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 11/765,716

(22) Filed: Jun. 20, 2007

(65) Prior Publication Data

US 2008/0033573 A1    Feb. 7, 2008

Related U.S. Application Data

(63) Continuation of application No. 10/935,353, filed on Sep. 7, 2004, now abandoned.

(60) Provisional application No. 60/504,355, filed on Sep. 19, 2003.

(51) Int. Cl.
| | |
|---|---|
| C08F 110/02 | (2006.01) |
| C08F 20/06 | (2006.01) |
| C08F 118/02 | (2006.01) |
| C08F 8/00 | (2006.01) |
| C08F 283/00 | (2006.01) |
| C08L 31/00 | (2006.01) |
| C08L 33/02 | (2006.01) |
| C08L 29/00 | (2006.01) |

(52) U.S. Cl. ............ 525/191; 525/220; 525/221; 525/231; 525/474; 526/352; 526/317.1; 526/319

(58) Field of Classification Search ............ 526/352, 526/317.1, 319; 525/191, 220, 221, 231, 525/474; D24/155
See application file for complete search history.

(56) References Cited

U.S. PATENT DOCUMENTS

| | | | |
|---|---|---|---|
| 3,297,805 | A | 1/1967 | Rottig et al. |
| 3,954,927 | A | 5/1976 | Duling et al. |
| 4,454,612 | A | 6/1984 | McDaniel et al. |
| 4,656,083 | A | 4/1987 | Hoffman et al. |
| 4,670,508 | A * | 6/1987 | Ohdaira et al. ............ 525/64 |
| 4,778,601 | A | 10/1988 | Lopatin et al. |
| 4,880,843 | A | 11/1989 | Stein |
| 4,919,659 | A | 4/1990 | Horbett et al. |
| 5,080,924 | A | 1/1992 | Kamel et al. |
| 5,275,838 | A | 1/1994 | Merrill |
| 5,413,760 | A | 5/1995 | Campbell et al. |
| 5,414,049 | A | 5/1995 | Sun et al. |
| 5,603,895 | A | 2/1997 | Martens et al. |
| 6,017,975 | A | 1/2000 | Saum et al. |
| 6,174,934 | B1 | 1/2001 | Sun et al. |
| 6,228,900 | B1 | 5/2001 | Shen et al. |
| 6,242,507 | B1 | 6/2001 | Saum et al. |
| 6,316,158 | B1 | 11/2001 | Saum et al. |
| 6,379,741 | B1 | 4/2002 | Komvopoulos et al. |
| 6,818,172 | B2 | 11/2004 | King et al. |
| 6,854,677 | B2 | 2/2005 | Sugawara |
| 7,214,764 | B2 | 5/2007 | King |
| 2002/0125614 | A1 | 9/2002 | King et al. |
| 2003/0083433 | A1 | 5/2003 | James et al. |
| 2003/0125513 | A1 | 7/2003 | King |
| 2003/0144741 | A1 | 7/2003 | King et al. |
| 2003/0144742 | A1 * | 7/2003 | King et al. ............ 623/23.58 |
| 2004/0210316 | A1 | 10/2004 | King et al. |
| 2004/0262809 | A1 | 12/2004 | Smith et al. |
| 2004/0265165 | A1 | 12/2004 | King |
| 2005/0065307 | A1 | 3/2005 | King et al. |
| 2005/0069696 | A1 | 3/2005 | King et al. |
| 2006/0004168 | A1 | 1/2006 | Greer et al. |
| 2006/0149387 | A1 | 7/2006 | Smith et al. |
| 2006/0149388 | A1 | 7/2006 | Smith et al. |

FOREIGN PATENT DOCUMENTS

| | | |
|---|---|---|
| DE | 227 328 A1 | 9/1985 |
| EP | 0 335 613 A2 | 10/1989 |
| WO | WO 85/04365 A1 | 10/1985 |
| WO | WO 86/02656 A1 | 5/1986 |
| WO | WO 93/25247 A1 | 12/1993 |
| WO | WO 03/057769 A1 | 7/2003 |

OTHER PUBLICATIONS

Bavaresco et al., "Devices for use as an artificial articular surface in joint prostheses or in the repair of osteochondral defects," *Artificial Organs*, 24 (3): 202-205 (Mar. 2000).

(Continued)

*Primary Examiner*—William K Cheung
(74) *Attorney, Agent, or Firm*—Leydig, Voit & Mayer, Ltd.

(57) ABSTRACT

The invention provides a medical implant or medical implant part comprising porous ultrahigh molecular weight polyethylene having a weight average molecular weight of about 400,000 atomic mass units or more and a porosity of about 15% to about 65%. The invention further provides a process for producing a medical implant or medical implant part.

15 Claims, 3 Drawing Sheets

OTHER PUBLICATIONS

Beauregard et al., "Synthesis and characterization of a novel UHMWPE interpenetrating polymer network," *Biomedical Sciences Instrumentation*, 35: 415-419 (Apr. 16, 1999).

King et al., "Hydrophilic, porous ultra-high molecular weight polyethylene for orthopaedic implants," *Transactions 7th World Biomaterials Congress*, 1909 (May 17021, 2004).

King et al., "Porous ultra-high molecular weight polyethylene scaffold for orthopaedic implants," *51st Annual Meeting of the Orthopaedic Research Society*, Poster No. 1682 (Feb. 2005).

Kurtz et al., "Advances in the processing, sterilization, and crosslinking of ultra-high molecular with polyethylene for total joint arthroplasty," *Biomaterials*, 20 (18): 1659-1688 (1999).

Shutov et al., "Cellular UHMW polyethylene produced by non-foaming leaching technique: morphology and properties," *Journal of Cellular Plastics*, 38, 163-176 (Mar. 2002).

Stein, "Ultra high molecular weight polyethylene (UHMWPE)", *Engineered Materials Handbook*, vol. 2: Engineering Plastics, pp. 167-171 (1998).

Zhang et al., "Surface modification of UHMWPE for use in total joint replacements," *Biomedical Science Instrumentation*, 40, 13-17 (ASM International, Materials Park, Ohio, US, 2004).

\* cited by examiner

MEDICAL IMPLANT OR MEDICAL IMPLANT PART COMPRISING POROUS UHMWPE AND PROCESS FOR PRODUCING THE SAME

CROSS-REFERENCE TO RELATED PATENT APPLICATIONS

This patent application is a continuation of copending U.S. patent application Ser. No. 10/935,353, filed Sep. 7, 2004, which claims the benefit of U.S. Provisional Patent Application No. 60/504,355, filed Sep. 19, 2003, which are incorporated herein by reference in their entirety.

FIELD OF THE INVENTION

This invention pertains to medical implants and medical implant parts comprising porous ultrahigh molecular weight polyethylene and processes for producing the same.

BACKGROUND OF THE INVENTION

The success of orthopaedic implants surgically implanted in living bone substantially depends on achieving and maintaining an enduring bond between the confronting surfaces of the implant and the host bone. Surgical procedures for preparing living bone to receive a surgically implanted orthopaedic device have been known for twenty years or more, but the ideal properties of the surface of the orthopaedic implant which confronts the host bone and processes of preparing the implant surface are the subjects of considerable disagreement.

Ultrahigh molecular weight polyethylene is widely used in the orthopaedics industry for the production of orthopaedic implants due to its relatively high wear-resistance and bio-compatibility. For example, ultrahigh molecular weight polyethylene frequently is used to produce the acetabular cup of artificial hip joints. However, virgin ultrahigh molecular weight polyethylene is bio-inert, and living cells (e.g., bone cells, osteoblast-like cells, or soft tissue cells) show relatively little, if any, affinity towards such virgin ultrahigh molecular weight polyethylene. Accordingly, orthopaedic implants comprising ultrahigh molecular weight polyethylene components that must be anchored to the host bone are at risk for potential failure of the orthopaedic implant unless additional means are undertaken to ensure the establishment and maintenance of a bond between the ultrahigh molecular weight polyethylene component and the host bone.

Many techniques have been or currently are used to establish such a bond between the ultrahigh molecular weight polyethylene component and the host bone. For instance, early ultrahigh molecular weight polyethylene components, such as the acetabular cup of an artificial hip, were bonded to the host bone (i.e., the acetabulum of the pelvis) using a bone cement. Currently, some commercially available ultrahigh molecular weight polyethylene components have been provided with complex surface geometries, which surface geometries comprise ridges and/or projections, intended to provide sites for the anchoring of the ultrahigh molecular weight polyethylene component to the host bone. Alternatively, ultrahigh molecular weight polyethylene components can be anchored to the host bone using a mechanical fastener or attached to a metallic "shell" or "tray," which shell or tray usually comprises a roughened and/or porous coating that confronts the host bone. While each of these means for effectively "bonding" the ultrahigh molecular weight polyethylene component to the host bone have enjoyed varying degrees of success, orthopaedic implants relying on such means are at risk for failure if the particular means (e.g., the ridge, protrusion, or mechanical fastener) fails.

A need therefore exists for a medical implant or medical implant part comprising ultrahigh molecular weight polyethylene that provides a substrate suitable for bone in-growth and/or soft tissue in-growth. A need also exists for a medical implant or medical implant part comprising ultrahigh molecular weight polyethylene having a structure that permits bone cement to penetrate into the medical implant or medical implant part, which can increase the strength of the bond between the medical implant or medical implant part and the host bone. The invention provides such an implant and a process for making the same. These and other advantages of the invention, as well as additional inventive features, will be apparent from the description of the invention provided herein.

BRIEF SUMMARY OF THE INVENTION

The invention provides a medical implant or medical implant part comprising porous ultrahigh molecular weight polyethylene, wherein (i) the ultrahigh molecular weight polyethylene has a weight average molecular weight of about 400,000 atomic mass units or more, (ii) the ultrahigh molecular weight polyethylene has a porosity of about 20% or more, (iii) the average diameter of the pores in the ultrahigh molecular weight polyethylene is about 400 μm or less, and (iv) at least some of the ultrahigh molecular weight polyethylene comprises hydrophilic functional groups attached thereto.

The invention also provides a medical implant or medical implant part comprising porous ultrahigh molecular weight polyethylene, wherein (i) the ultrahigh molecular weight polyethylene has a weight average molecular weight of about 400,000 atomic mass units or more, (ii) the ultrahigh molecular weight polyethylene has a porosity of about 15% to about 65%, and (iii) at least about 5% (by volume) of the pores in the ultrahigh molecular weight polyethylene have a diameter of about 200 μm or more.

The invention further provides a process for producing a medical implant or medical implant part comprising porous ultrahigh molecular weight polyethylene, the process comprising: (a) providing a compression mold for the medical implant or medical implant part having an internal volume, (b) providing a matrix comprising ultrahigh molecular weight polyethylene, wherein the ultrahigh molecular weight polyethylene has a weight average molecular weight of about 400,000 atomic mass units or more, (c) dispersing a porogen comprising a melt-processable polymer in the matrix to produce a mixture comprising at least one porogen and ultrahigh molecular weight polyethylene, (d) filling at least a portion of the internal volume of the compression mold with the mixture obtained in step (c), (e) compressing the mixture contained within the compression mold for a time and under conditions sufficient to form a medical implant or medical implant part therefrom, (f) removing the medical implant or medical implant part from the compression mold, and (g) immersing the medical implant or medical implant part obtained in step (f) in a solvent for a time and under conditions sufficient to extract at least a portion of the porogen from the medical implant or medical implant part.

DETAILED DESCRIPTION OF THE INVENTION

Figure 1:
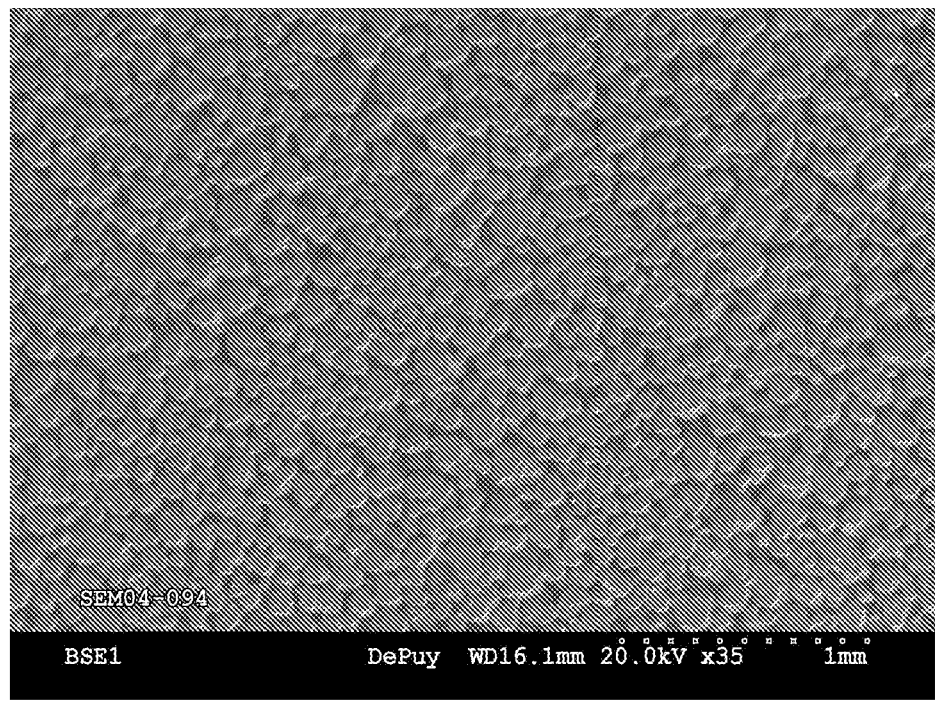
FIG. 1 is a Scanning Electron Microscopy (SEM) micrograph (35 times magnification) of the surface of porous ultrahigh molecular weight polyethylene (porosity of about 23%) made by a conventional sintering process.

The invention provides a medical implant or medical implant part comprising porous ultrahigh molecular weight polyethylene. The medical implant or medical implant part can be any suitable medical implant or medical implant part. Suitable medical implants or medical implant parts include, but are not limited to, the acetabular cup, the insert or liner of the acetabular cup, or trunnion bearings of artificial hip joints, the tibial plateau, patellar button (patello-femoral articulation), and trunnion or other bearing components of artificial knee joints, the talar surface (tibiotalar articulation) and other bearing components of artificial ankle joints, the radio-numeral joint, ulno-humeral joint, and other bearing components of artificial elbow joints, the glenoro-humeral articulation and other bearing components of artificial shoulder joints, intervertebral disk replacements and facet joint replacements for the spine, temporo-mandibular joints (jaw), and finger joints. Alternatively, the medical implant or medical implant part can be a drug delivery device that is adapted to be implanted within a host. In such an embodiment, the medical implant or medical implant part can comprise one or more active ingredients, for example, contained in the pores of the ultrahigh molecular weight polyethylene.

As noted above, the medical implant or medical implant part comprises ultrahigh molecular weight polyethylene. Preferably, the ultrahigh molecular weight polyethylene has a weight average molecular weight of about 400,000 atomic mass units or more, more preferably about 1,000,000 (e.g., about 2,000,000 or about 3,000,000) atomic mass units or more. Typically, the weight average molecular weight of the ultrahigh molecular weight polyethylene is about 10,000,000 atomic mass units or less, more preferably about 6,000,000 atomic mass units or less. Ultrahigh molecular weight polyethylene suitable for use in the invention includes, but is not limited to, commercially available ultrahigh molecular weight polyethylene, such as GUR 1050 powdered ultrahigh molecular weight polyethylene (weight average molecular weight of about 4,000,000 to about 6,000,000 atomic mass units) and GUR 1020 powdered ultrahigh molecular weight polyethylene (weight average molecular weight of about 2,000,000 to about 4,000,000 atomic mass units) from Ticona (Summit, N.J.). Preferably, the ultrahigh molecular weight polyethylene does not contain stabilizers, antioxidants, or other chemical additives which may have potential adverse effects in medical applications.

The medical implant or medical implant part comprises ultrahigh molecular weight polyethylene that is porous. As utilized herein, the term "porous" refers to a mass of ultrahigh molecular weight polyethylene comprising open pores on at least a portion of its exterior surface. The ultrahigh molecular weight polyethylene preferably comprises pores distributed throughout the mass. The pores can be distributed throughout the ultrahigh molecular weight polyethylene in any suitable manner. In certain embodiments, the pores are concentrated at or near the surface of the ultrahigh molecular weight polyethylene. Preferably, the pores are substantially uniformly distributed throughout the ultrahigh molecular weight polyethylene comprising the medical implant or medical implant part of the invention. Preferably, at least a portion of the pores present in the ultrahigh molecular weight polyethylene are interconnected (i.e., the pores are connected to one or more of the adjacent pores).

The ultrahigh molecular weight polyethylene can have any suitable porosity. As utilized herein, the term "porosity" refers to the ratio of the total volume of the pores (e.g., void volume) in the ultrahigh molecular weight polyethylene to the overall volume of the ultrahigh molecular weight polyethylene. Preferably, the ultrahigh molecular weight polyethylene has a porosity of about 15% or more, more preferably about 20% or more, even more preferably about 25% or more (e.g., about 30% or more or about 35% or more). It will be understood that, as the porosity of the ultrahigh molecular weight polyethylene increases, the mechanical strength of the medical implant or medical implant part can decrease. Accordingly, the porosity of the ultrahigh molecular weight polyethylene preferably is not so high as to substantially compromise the mechanical strength of the medical implant or medical implant part. To that end, the ultrahigh molecular weight polyethylene typically has a porosity of about 65% or less (e.g., about 60% or less), preferably about 55% or less, more preferably about 50% or less (e.g., about 45% or less or about 40% or less). In a preferred embodiment, the ultrahigh molecular weight polyethylene has a porosity of about 20% to about 50%.

The pores present in the ultrahigh molecular weight polyethylene can have any suitable diameter. Preferably, at least a portion of the pores in the ultrahigh molecular weight polyethylene have a diameter of about 200 μm or more (e.g., about 250 μm or more, about 300 μm or more, or about 350 μm or more). Any suitable percentage of the pores can have a diameter falling within one of the above-recited ranges (e.g., about 200 μm or more). Indeed, it will be understood that the preferred percentage of pores in the ultrahigh molecular weight polyethylene having a diameter falling within one of the above-recited ranges will depend, at least in part, on the intended use of the medical implant or medical implant part. Accordingly, the preferred percentage for a medical implant or medical implant part that will be fixated using a bone cement may be different from the preferred percentage for a medical implant or medical implant part that will be fixated using a press-fit technique, in which the medical implant or medical implant part is anchored to the host bone by osseointegration and/or soft tissue attachment. Preferably, the percentage (by volume) of pores having a diameter falling within one of the above-recited ranges (e.g., having a diameter of about 200 μm or more) is about 5% or more (e.g., about 10% or more, or about 15% or more), more preferably about 25% or more (e.g., about 35% or more, about 40% or more, or about 50% or more). Typically, the percentage (by volume) of pores having a diameter falling within one of the above-recited ranges (e.g., having a diameter of about 200 μm or more or about 200 μm to about 800 μm) will not exceed about 85% (e.g., will not exceed about 80%). The percentage (by volume) of pores having a particular diameter can be determined using any suitable technique. Preferably, the percentage (by volume) of pores falling within any of the ranges recited herein is determined using mercury intrusion porosimetry, for example, using a PoreMaster® 33 automatic pore size analyzer from Quantachrome Instruments (Boynton Beach, Fla.).

Generally, the average diameter of the pores in the ultrahigh molecular weight polyethylene is about 400 μm or less. It will be understood that the preferred diameter of the pores in the ultrahigh molecular weight polyethylene will depend, at least in part, on the intended use of the medical implant or medical implant part. Accordingly, the preferred average pore diameter for a medical implant or medical implant part that will be fixated using a bone cement may be different from the preferred average pore diameter for a medical implant or medical implant part that will be fixated using a press-fit technique, in which the medical implant or medical implant part is anchored to the host bone by osseointegration and/or soft tissue attachment. Preferably, the average diameter of the pores in the ultrahigh molecular weight polyethylene is about 350 μm or less, more preferably about 300 μm or less (e.g., about 250 μm or less). The average diameter of the pores in the ultrahigh molecular weight polyethylene typically is about 1 μm or more, preferably about 10 μm or more, more preferably about 25 μm or more, and most preferably about 50 μm or more (e.g., about 75 μm or more, or about 100 μm or more). The average diameter of the pores can be determined using any suitable technique. Preferably, the average diameter of the pores is determined using mercury intrusion porosimetry, for example, using a PoreMaster® 33 automatic pore size analyzer from Quantachrome Instruments (Boynton Beach, Fla.).

Preferably, at least a portion (e.g., at least a portion of the surface) of the porous ultrahigh molecular weight polyethylene is hydrophilic. It will be understood that, when referring to the ultrahigh molecular weight polyethylene, the term "hydrophilic" is used to refer to ultrahigh molecular weight polyethylene that is more hydrophilic than similar, "untreated" ultrahigh molecular weight polyethylene. The ultrahigh molecular weight polyethylene can be made hydrophilic by any suitable means. In certain embodiments, the ultrahigh molecular weight polyethylene comprises hydrophilic functional groups attached to at least a portion thereof. The hydrophilic functional groups can be directly attached to at least a portion of the ultrahigh molecular weight polyethylene, or the hydrophilic functional groups can be part of hydrophilic monomers attached to at least a portion of the ultrahigh molecular weight polyethylene. Preferably, the hydrophilic functional groups comprise one or more functional groups selected from the group consisting of amino functional groups, carboxylic acid functional groups, hydroxyl functional groups, hydroxysulfuryl functional groups, and combinations thereof. More preferably, the hydrophilic functional groups comprise one or more carboxylic acid functional groups. Suitable hydrophilic monomers that can be used to modify the surface of the ultrahigh molecular weight polyethylene include, but are not limited to, acrylic acid, poly(ethylene glycol), 2-hydroxyethyl methacrylate, and combinations thereof.

While not wishing to be bound to any particular theory, it is believed that the porous and/or hydrophilic nature of the ultrahigh molecular weight polyethylene of the medical implant or medical implant part provides an ideal substrate for bone in-growth, soft tissue in-growth, and/or penetration of bone cement. More specifically, it is believed that the porous nature of the ultrahigh molecular weight polyethylene provides a featured surface to which cells (e.g., bone cells, osteoblast-like cells, or soft tissue cells) can attach themselves. Furthermore, when the ultrahigh molecular weight polyethylene of the medical implant or medical implant part comprises hydrophilic functional groups, it is believed that the hydrophilicity of the ultrahigh molecular weight polyethylene attracts and further promotes the attachment of cells as compared to untreated ultrahigh molecular weight polyethylene. It is also believed that the porous nature of the ultrahigh molecular weight polyethylene allows bone cement to penetrate, at least partially, into the interior portions of the medical implant or medical implant part, thereby improving the ability of the bone cement to anchor the medical implant or medical implant part to the host bone. For example, it is believed that the porous nature of the ultrahigh molecular weight polyethylene can allow the monomer(s) of the bone cement to diffuse into the interior portions of the medical implant or medical implant part, where they can be polymerized to form a polymer network distributed throughout the porous structure of the ultrahigh molecular weight polyethylene. Such a network of the bone cement can provide a link or connection between the interior portions of the medical implant or medical implant part and the bone cement on the exterior portions of the medical implant or medical implant part (e.g., the bone cement confronting the host bone).

The invention further provides a process for producing a medical implant or medical implant part comprising porous ultrahigh molecular weight polyethylene, the process comprising: (a) providing a compression mold for the medical implant or medical implant part having an internal volume, (b) providing a matrix comprising ultrahigh molecular weight polyethylene, wherein the ultrahigh molecular weight polyethylene has a weight average molecular weight of about 400,000 atomic mass units or more, (c) dispersing a porogen comprising a melt-processable polymer in the matrix to produce a mixture comprising at least one porogen and ultrahigh molecular weight polyethylene, (d) filling at least a portion of the internal volume of the compression mold with the mixture obtained in step (c), (e) compressing the mixture contained within the compression mold for a time and under conditions sufficient to form a medical implant or medical implant part therefrom, (f) removing the medical implant or medical implant part from the compression mold, and (g) immersing the medical implant or medical implant part obtained in step (f) in a solvent for a time and under conditions sufficient to extract at least a portion of the porogen from the medical implant or medical implant part.

The characteristics of the medical implant or medical implant part produced by the method of the invention (e.g., the molecular weight of the ultrahigh molecular weight polyethylene, the porosity of the ultrahigh molecular weight polyethylene, the size and/or shape of the pores, etc.) can be the same as those set forth above for the medical implant or medical implant part of the invention.

As noted above, the method of the invention comprises providing a compression mold for the medical implant or medical implant part having an internal volume. The term "compression mold" is utilized herein to refer to a mold typically having two halves which, when joined together, define an internal volume (i.e., mold cavity). The compression mold can be provided in any suitable configuration. Generally, the compression mold is configured such that the internal volume of the compression mold (i.e., the mold cavity) defines the medical implant or medical implant part in a substantially complete form (i.e., in substantially the same form as will be used for implantation in the host). However, it will be understood that the medical implant or medical implant part produced by the method of the invention also can be subjected to further processing (e.g., machining) to provide the medical implant or medical implant part in the final form used for implantation in the host.

The matrix of ultrahigh molecular weight polyethylene can be provided in any suitable form. Preferably, the matrix of ultrahigh molecular weight polyethylene comprises, consists essentially of, or consists of ultrahigh molecular weight polyethylene in a powdered or pelletized form.

As noted above, the method of the invention utilizes a porogen. As utilized herein, the term "porogen" refers to a labile, pore-generating material (i.e., a material capable of readily undergoing, under the appropriate conditions, chemical and/or physical changes to form pores in the ultrahigh molecular weight polyethylene). Preferably, the porogen comprises a melt-processable polymer. As utilized herein to refer to the melt-processable polymer present in the porogen, the term "melt-processable" refers to a polymer that can be processed in its molten state using processes such as injection molding, extrusion molding, blow molding, and/or compression molding. Preferably, a melt processable polymer does not exhibit significant oxidative degradation, decomposition, or pyrolysis at the processing temperatures typically used in such molding processes. The porogen can comprise any suitable melt-processable polymer. Suitable melt-processable polymers include, but are not limited to, poly(ethylene oxide), polyethylene glycol, polyethylene glycol copolymers (e.g., poly(ethylene glycol)-poly(propylene glycol) copolymers, poly(ethylene glycol)-poly(propylene glycol)-poly(ethylene glycol) block copolymers, or poly(propylene glycol)-poly(ethylene glycol)-poly(propylene glycol) block copolymers), poly(propylene glycol), poly(2-hydroxyethyl methacrylate), poly(vinyl alcohol), poly(acrylic acid), poly(methacrylic acid), polyvinylpyrrolidone, cellulose ether, alginate, chitosan, hyaluronate, collagen, and mixtures or combinations thereof. Preferably, the melt-processable polymer is selected from the group consisting of polyethylene glycol, poly(ethylene oxide), polyvinylpyrrolidone, poly(vinyl alcohol), and mixtures thereof. In certain embodiments, the melt-processable polymer preferably is water-soluble. As utilized herein, the term "water-soluble" refers to a polymer having a solubility in water (at 25° C.) of about 1 mg/L or more, preferably about 10 mg/L or more, more preferably about 30 mg/L or more, even more preferably about 100 mg/L or more, and most preferably about 1,000 mg/L or more.

In order to ensure that the melt-processable polymer remains distributed throughout the ultrahigh molecular weight polyethylene during the compression molding step of the inventive process, the melt-processable polymer preferably has a low melt index. Typically, the melt-processable polymer has a melt index of about 5 g/10 min or less (i.e., equal to or less than about 5 g/10 min), such as about 4 g/10 min or less, about 3 g/10 min or less, about 2 g/10 min or less, or about 1 g/10 min or less (e.g., about 0.1 g/10 min to about 1 g/10 min). Preferably, the melt-processable polymer has a melt index of about 0.5 g/10 min or less, more preferably about 0.45 g/10 min or less, even more preferably about 0.425 g/10 min or less, and most preferably about 0.4 g/10 min or less.

The melt index of the melt-processable polymer can be determined using any suitable method. Preferably, the melt index of the melt-processable polymer is determined in accordance with ASTM Standard D1238-88 (entitled, "Flow Rates of Thermoplastics by Extrusion Plastometer") using the following conditions: (i) 190° C., (ii) 21.6 kg weight, (iii) 20 cm$^3$ sample, and (iv) 5.5 minute preheat time. More specifically, the equipment used to determine the melt index of the melt-processable polymer (i.e., the plastometer, the cylinder, the die, the piston, the heater, the thermometer, etc.) is the same as that defined in ASTM Standard D1238-88; however, the conditions under which the melt index is measured differ from those specified in the aforementioned standard. In particular, a 20 cm$^3$ sample of the melt-processable polymer, which sample is provided as a homogeneous powder or pellets, is used to determine the melt index of the melt-processable polymer. The 20 cm$^3$ sample is placed in the barrel of the plastometer while tamping the material to ensure that the entire sample is placed in the barrel and at least 90% of the volume of the barrel is filled with the sample. After the sample is loaded into the barrel of the plastometer, the piston is inserted into the barrel, and 10.8 kg of weight is placed on the piston. The timing of the 5.5 minute preheating cycle is then begun. During the preheat cycle, the weight on the piston is adjusted so that the sample extrudes from the barrel at a rate such that the lower two scribed marker lines on the piston reach the top of the barrel by the end of the 5.5 minute preheat cycle (+/−15 seconds). Immediately prior to the completion of the preheat cycle, the weight on the piston is increased to 21.6 kg. Once the lower of the two scribed marker lines on the piston reaches the top of the barrel, the extrudate is cut from the barrel, and a timed sampling cycle is begun. Typically, the sampling cycle is about 1 minute; however, the length of the sampling cycle can be shorter (e.g., 30 seconds) or longer (e.g., 2 minutes) depending on the rate at which the sample extrudes from the barrel of the plastometer. At the end of the sampling cycle, the extrudate is cut from the barrel and weighed. The melt index (in g/10 min) is then calculated using the weight of the extrudate and the duration of the sampling cycle.

In addition to the melt-processable polymer, the porogen can also comprise other suitable labile, pore-generating materials. Such materials include, but are not limited to, hydrocarbons (e.g., aliphatic, cyclic, and aromatic hydrocarbons), waxes (e.g., polyethylene waxes, paraffin waxes, and synthetic waxes), and soluble salts (e.g., sodium chloride). Typically, in order to lessen the risk of adverse reactions following implantation of the medical implant or medical implant part, it is desirable to avoid the use of organic solvents in preparing the medical implant or medical implant part of the invention. Accordingly, any additional materials included in the porogen preferably are water-soluble. Suitable water-soluble porogens include, but are not limited to, water-soluble salts, such as sodium chloride or potassium chloride.

When the porogen comprises a mixture of a melt-processable polymer and another labile, pore-generating material, the melt-processable polymer can comprise any suitable portion of the total volume of the porogen. The melt-processable polymer typically comprises about 5 vol. % or more, preferably about 10 vol. % or more, more preferably about 15 vol. % or more (e.g., about 20 vol. % or more) of the total volume of the porogen. Typically, the melt-processable polymer comprises about 50 vol. % or less, preferably about 45 vol. % or less, more preferably about 40 vol. % or less (e.g., about 35 vol. % or less, or about 33 vol. % or less) of the total volume of the porogen.

The porogen is dispersed in the matrix of ultrahigh molecular weight polyethylene to produce a mixture comprising at least one porogen and ultrahigh molecular weight polyethylene. In a preferred embodiment, the mixture consists essentially of, or consists of, the porogen and ultrahigh molecular weight polyethylene. The porogen can be dispersed in the ultrahigh molecular weight polyethylene using any suitable means. Typically, the porogen and the ultrahigh molecular weight polyethylene are provided in a powdered or pelletized form, and the porogen is dispersed in the ultrahigh molecular weight polyethylene by dry blending the two components to form a mixture comprising the porogen and ultrahigh molecular weight polyethylene. The porogen and ultrahigh molecular weight polyethylene can be dry blended using any suitable apparatus, such as the Turbula® shaker-mixers manufactured by Glen Mills Inc. (Clifton, N.J.).

As noted above, at least a portion of the internal volume of the compression mold (i.e., mold cavity) is filled with the mixture comprising, consisting essentially of, or consisting of the porogen and ultrahigh molecular weight polyethylene. Preferably, the portion of the internal volume of the compression mold filled with the mixture comprises a portion of a surface layer of the medical implant or medical implant part. In such an embodiment, the surface layer preferably corresponds to a surface of the medical implant or medical implant part that, after implantation into the host, is adjacent to (e.g., abuts) bone and/or soft tissue. In another embodiment, substantially all of the internal volume of the compression mold preferably is filled with the mixture comprising the porogen and ultrahigh molecular weight polyethylene. When only a portion of the internal volume of the compression mold is filled with the mixture comprising the porogen and ultrahigh molecular weight polyethylene, the remaining portion of the internal volume of the compression mold preferably is filled with ultrahigh molecular weight polyethylene.

After at least a portion of the internal volume of the compression mold is filled, the mixture comprising the porogen and ultrahigh molecular weight polyethylene contained within the compression mold is compressed for a time and under conditions sufficient to form a medical implant or medical implant part therefrom. It will be understood that the mixture comprising the porogen and ultrahigh molecular weight polyethylene is compressed by any suitable means, such as by mating the two halves of a two-part compression mold and applying an external force in a direction such that any substance contained within the mold (e.g., mixture comprising the porogen and ultrahigh molecular weight polyethylene) is subjected to a compressive force. It will be further understood that the particular time and conditions (e.g., force applied to the compression mold) necessary to form a medical implant or medical implant part will depend upon several factors, such as the composition of the mixture (i.e., the type and/or amount of porogen(s) added to the mixture), and the size (e.g., thickness) of the desired medical implant or medical implant part, as well as other factors. Typically, the mixture is subjected to a pressure of about 3,400 kPa to about 28,000 kPa during the compression molding step. Preferably, the mixture is subjected to a pressure of about 3,400 kPa to about 14,000 kPa (e.g., about 3450 kPa to about 6,900 kPa) or about 3,800 kPa to about 14,000 kPa. During the compression molding step, the mixture typically is subjected to a temperature of about 140° C. to about 220° C. at a heating rate of about 5° C./min to about 12° C./min. Preferably, the mixture is subjected to a temperature of about 160° C. to about 210° C. (e.g., about 160° C. to about 200° C.), more preferably a temperature of about 170° C. to about 190° C., during the compression molding step. The mixture can be compressed in the compression mold for any amount of time sufficient to form a medical implant or medical implant part therefrom. Typically, the mixture is compressed for about 5 to about 30 minutes, more preferably about 5 to about 20 minutes (e.g., about 15 minutes), during the compression molding step. Once the mixture has been compressed for the desired amount of time, the resulting medical implant or medical implant part typically is cooled (e.g., to a temperature of about 38° C. (100° F.)) at a rate of about 2° C./min to about 6° C./min.

The invention further comprises the step of (g) immersing the medical implant or medical implant part obtained in step (f) in a solvent for a time and under conditions sufficient to extract at least a portion of the porogen from the medical implant or medical implant part. Preferably, the medical implant or medical implant part is immersed in the solvent for a time and under conditions to remove substantially all of the porogen (e.g., about 90% or more, about 95% or more, or about 98% or more). It will be understood that the particular solvent used to remove (e.g., extract) the porogen from the medical implant or medical implant part will depend, at least in part, on the particular porogen used. Furthermore, it will be understood that the particular solvent used to remove (e.g., extract) the porogen from the medical implant or medical implant part should not damage (e.g., significantly swell and/or dissolve) the ultrahigh molecular weight polyethylene of the medical implant or medical implant part. In certain embodiments, such as when the porogen is water-soluble (e.g., the porogen comprises a water-soluble, melt-processable polymer), the solvent preferably comprises or is water. In other embodiments, the solvent can comprise a mixture of two or more different solvents. For example, the solvent can comprise a mixture of water and a polar, bio-inert, organic solvent. Suitable polar, bio-inert, organic solvents include, but are not limited to, ethyl acetate, ethanol, acetone, methyl ethyl ketone, N-methyl-2-pyrrolidone. Alternatively, the medical implant or medical implant part can be sequentially immersed in two or more different solvents (e.g., a first solvent comprising, consisting essentially of, or consisting of water and a second solvent comprising, consisting essentially of, or consisting of ethyl acetate).

The medical implant or medical implant part can be immersed in the solvent for any suitable amount of time and under any conditions suitable for the extraction of at least a portion of the porogen from the medical implant or medical implant part. For example, the medical implant or medical implant part typically is immersed in the solvent for up to about 170 hours, preferably for about 48 hours to about 170 hours. The solvent can be maintained at any suitable temperature during the extraction step. It will be understood that the particular temperature at which the solvent is maintained during the extraction step will depend, at least in part, on the particular solvent(s) used, as well as the composition of the porogen. In certain embodiments, such as when the solvent comprises water, the solvent typically is maintained at a temperature of about 20° C. to about 100° C., preferably about 20° C. to about 60° C. (e.g., about 20° C. to about 30° C.). During the extraction step, one or more nozzles can be used to generate jet(s) of the solvent that are sprayed onto the surface of the medical implant or medical implant part under pressure (e.g., at a pressure of about 350 kPa or less). The extraction process can additionally or alternatively comprise the step of passing ultrasonic waves through solvent (e.g., by immersing the medical implant or medical implant part in a solvent contained in a suitable ultrasonic bath).

The process of the invention optionally, but preferably, further comprises the step of (h) modifying at least a portion of the ultrahigh molecular weight polyethylene to make the ultrahigh molecular weight polyethylene hydrophilic. The ultrahigh molecular weight polyethylene can be modified at any suitable point in time. Preferably, the ultrahigh molecular weight polyethylene contained within the medical implant or medical implant part is modified after the desired amount of the porogen has been extracted therefrom. The ultrahigh molecular weight polyethylene can be modified using any suitable method. Preferably, the ultrahigh molecular weight polyethylene is modified by introducing hydrophilic functional groups onto at least the ultrahigh molecular weight polyethylene exposed on the surface of the medical implant or medical implant part. The hydrophilic functional groups can be introduced onto the ultrahigh molecular weight polyethylene using any suitable method. For example, the hydrophilic functional groups can be directly introduced onto the ultrahigh molecular weight polyethylene, or the hydrophilic functional groups can be introduced onto the ultrahigh molecular weight polyethylene by grafting hydrophilic monomers (e.g., monomers containing one or more hydrophilic functional groups) onto the ultrahigh molecular weight polyethylene. The hydrophilic functional groups preferably comprise one or more functional groups selected from the group consisting of amino functional groups, carboxylic acid functional groups, hydroxyl functional groups, hydroxysulfuryl functional groups, and combinations thereof. More preferably, the hydrophilic functional groups comprise one or more carboxylic acid functional groups. Preferably, the ultrahigh molecular weight polyethylene is modified using a gas plasma method, such as the methods set forth in U.S. Pat. Nos. 4,656,083, 4,919,659, 5,080,924, and 6,379,741.

In certain embodiments, the process of the invention further comprises the step of irradiating the medical implant or medical implant part for a time and under conditions sufficient to cross-link at least a portion of the ultrahigh molecular weight polyethylene contained in the medical implant or medical implant part. The medical implant or medical implant part can be irradiated at any suitable point in time. Preferably, the medical implant or medical implant part is irradiated after the porogen has been removed from the medical implant or medical implant part. While not wishing to be bound to any particular theory, it is believed that removing the porogen from the medical implant or medical implant part before irradiating the ultrahigh molecular weight polyethylene increases the amount of porogen that can be removed from the medical implant or medical implant part. The medical implant or medical implant part also is preferably irradiated before the ultrahigh molecular weight polyethylene contained within the medical implant or medical implant part is modified to make the ultrahigh molecular weight polyethylene hydrophilic. While not wishing to be bound to any particular theory, it is believed that irradiating the medical implant or medical implant part before modification of the ultrahigh molecular weight polyethylene reduces the potential negative effects of chain-scission and/or free radical generation in the ultrahigh molecular weight polyethylene caused by the irradiation process.

The medical implant or medical implant part can be irradiated by any suitable means, such as by exposing the medical implant or medical implant part to a suitable amount of gamma, x-ray, or electron beam radiation. Preferably, medical implant or medical implant part is irradiated by exposure to about 0.5 to about 10 Mrad (e.g., about 1.5 to about 6 Mrad) of gamma radiation using methods known in the art. While the medical implant or medical implant part can be exposed to amounts of radiation falling outside of the aforementioned range, such amounts of radiation tend to produce a medical implant or medical implant part with unsatisfactory properties. In particular, radiation doses of less than about 0.5 Mrad generally provide insufficient cross-linking of the ultrahigh molecular weight polyethylene. Furthermore, while doses of greater than 10 Mrad may be used, the additional cross-linking that is achieved generally is offset by the increased brittleness of portions of the medical implant or medical implant part (e.g., the surface layer of the medical implant or medical implant part).

When irradiated, the medical implant or medical implant part preferably is irradiated in an inert or reduced-pressure atmosphere. Irradiating the medical implant or medical implant part in an inert (i.e., non-oxidizing) or reduced-pressure atmosphere reduces the effects of oxidation and chain scission reactions which can occur during irradiation in an oxidative atmosphere. Typically, the medical implant or medical implant part is placed in an oxygen-impermeable package during the irradiation step. Suitable oxygen-impermeable packaging materials include, but are not limited to, aluminum, polyester-coated metal foil (e.g., the Mylar® product available from DuPont Teijin Films), polyethylene terephthalate, and poly(ethylene vinyl alcohol). In order to further reduce the amount of oxidation which occurs during the irradiation of the medical implant or medical implant part, the oxygen-impermeable packaging may be evacuated (e.g., the pressure within the packaging may be reduced below the ambient atmospheric pressure) and/or flushed with an inert gas (e.g., nitrogen, argon, helium, or mixtures thereof) after the medical implant or medical implant part has been placed therein.

When the medical implant or medical implant part is irradiated, the free radicals generated in the ultrahigh molecular weight polyethylene preferably are quenched following the irradiation of the medical implant or medical implant part using methods known in the art. For example, the free radicals contained within the irradiated portion of the medical implant or medical implant part can be quenched by heating the irradiated medical implant or medical implant part to a temperature between room temperature and the melting point of ultrahigh molecular weight polyethylene in an oxygen-reduced, non-reactive atmosphere for a length of time sufficient to reduce the number of free radicals present in the medical implant or medical implant part (see, e.g., U.S. Pat. Nos. 5,414,049, 6,174,934, and 6,228,900). Alternatively, the free radicals contained within the irradiated portion of the medical implant or medical implant part can be quenched by heating the irradiated medical implant or medical implant part to a temperature at or above the melting point of ultrahigh molecular weight polyethylene in an oxygen-reduced, non-reactive atmosphere for a length of time sufficient to reduce the number of free radicals present in the medical implant or medical implant part (see, e.g., U.S. Pat. Nos. 6,017,975, 6,228,900, 6,242,507, and 6,316,158). Lastly, the free radicals contained within the irradiated portion of the medical implant or medical implant part can be quenched by immersing the irradiated portion of the medical implant or medical implant part in a non-polar solvent for a time and under conditions sufficient to quench a substantial portion of the free radicals contained therein. The aforementioned process is explained more fully in copending U.S. patent application Ser. Nos. 10/609,749 and 10/795,755.

The method of the invention can further comprise the steps of sterilizing the medical implant or medical implant part by any suitable means, preferably using a non-irradiative process. The medical implant or medical implant part can be sterilized at any suitable point in time, but preferably is sterilized after the completion of step (g) or step (h). Sterilizing the medical implant or medical implant part using a non-irradiative method avoids the formation of additional free radicals in the ultrahigh molecular weight polyethylene, which free radicals could undergo oxidative reactions resulting in the chain scission of the ultrahigh molecular weight polyethylene. Suitable non-irradiative sterilization techniques include, but are not limited to, gas plasma or ethylene oxide methods known in the art. For example, the packaged medical implant or packaged medical implant part can be sterilized using a PlazLyte® Sterilization System (Abtox, Inc., Mundelein, Ill.) or in accordance with the gas plasma sterilization processes described in U.S. Pat. Nos. 5,413,760 and 5,603,895.

The medical implant or medical implant part can be packaged in any suitable packaging material. Desirably, the packaging material maintains the sterility of the medical implant or medical implant part until the packaging material is breached. If the medical implant or medical implant part has not been irradiated or if the medical implant or medical implant part has been irradiated and a substantial portion of the free radicals contained within the medical implant or medical implant part have been quenched, the medical implant or medical implant part will be relatively stable to atmospheric oxidation. Under such circumstances, it would not be necessary to package the medical implant or medical implant part in an inert atmosphere and, therefore, the medical implant or medical implant part could be packaged in an air-impermeable or air-permeable packaging material.

Example

This example further illustrates the invention but, of course, should not be construed as in any way limiting its scope. This example demonstrates a process for producing a medical implant or medical implant part according to the invention, as well as the properties of the medical implant or medical implant part of the invention. Three samples of porous ultrahigh molecular weight polyethylene (Samples 1-3) were prepared from GUR 1020 powdered ultrahigh molecular weight polyethylene using three different processes.

Sample 1 (comparative) was prepared by a sintering process in which 14 grams of GUR 1020 powdered ultrahigh molecular weight polyethylene was placed into a cylindrical mold (approximately 10 cm in diameter) and heated in a high-vacuum oven to a temperature of approximately 200° C. under a load of approximately 5.6 kg for 180 minutes. The resulting sample was measured and weighed to determine its porosity, which was determined to be approximately 23%. The surface of the sample was then analyzed using a Hitachi S3500 N variable pressure scanning electron microscope and Quartz PCI image acquisition software (Version 4.1). An SEM micrograph (35× magnification) of the surface of Sample 1 is provided in FIG. 1.

Figure 2:
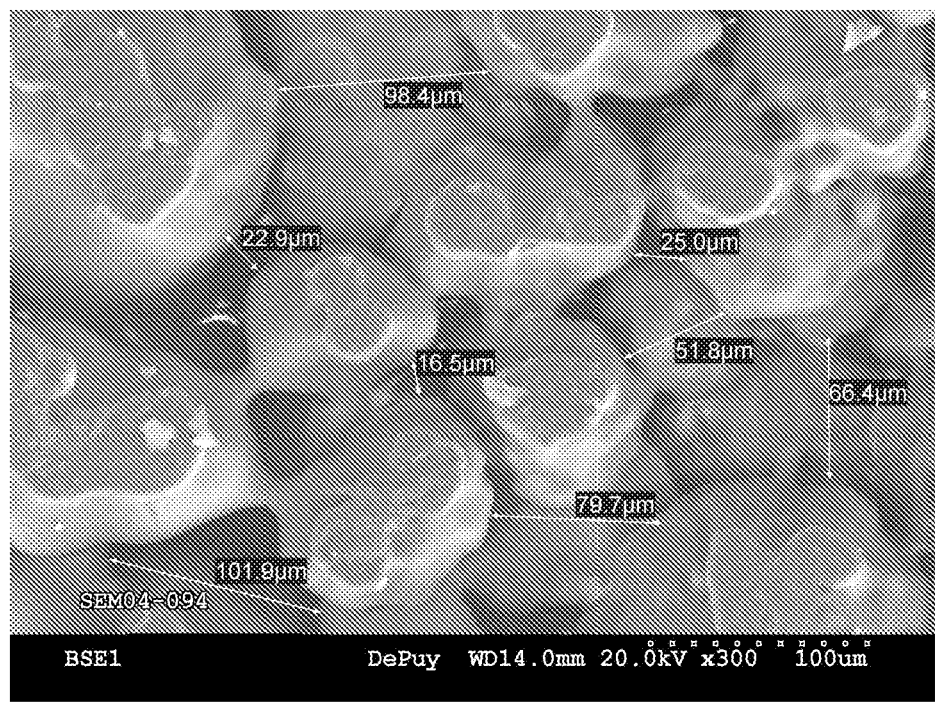
FIG. 2 is an SEM micrograph (300 times magnification) of the surface of porous ultrahigh molecular weight polyethylene (porosity of about 33%) made by a conventional sintering process. The micrograph also includes measurements of some of the pores present in the porous ultrahigh molecular weight polyethylene.

Sample 2 (comparative) was prepared by a sintering process in which 14 grams of GUR 1020 powdered ultrahigh molecular weight polyethylene was placed into a cylindrical mold (approximately 10 cm in diameter) and heated in a high-vacuum oven to a temperature of approximately 150° C. under a load of approximately 2.4 kg for 180 minutes. The resulting sample was measured and weighed to determine its porosity, which was determined to be approximately 33%. The surface of the sample was then analyzed using SEM. An SEM micrograph (300× magnification) of the surface of Sample 2 is provided in FIG. 2. The SEM micrograph was further analyzed using the Quartz PCI image acquisition software to determine the diameter of the pores present on the surface of the sample. The pore diameter measurements for selected pores are provided in FIG. 2.

Figure 3:
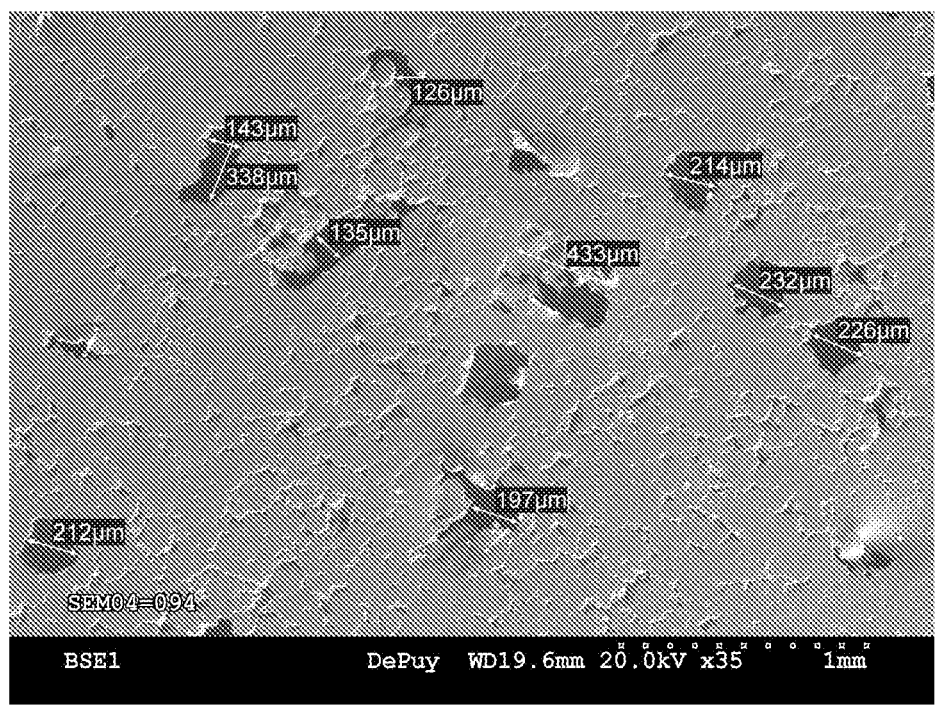
FIG. 3 is an SEM micrograph (35 times magnification) of the surface of porous ultrahigh molecular weight polyethylene (porosity of about 30%) made using the process of the invention. The micrograph also includes measurements of some of the pores present in the porous ultrahigh molecular weight polyethylene.
Figure 4:
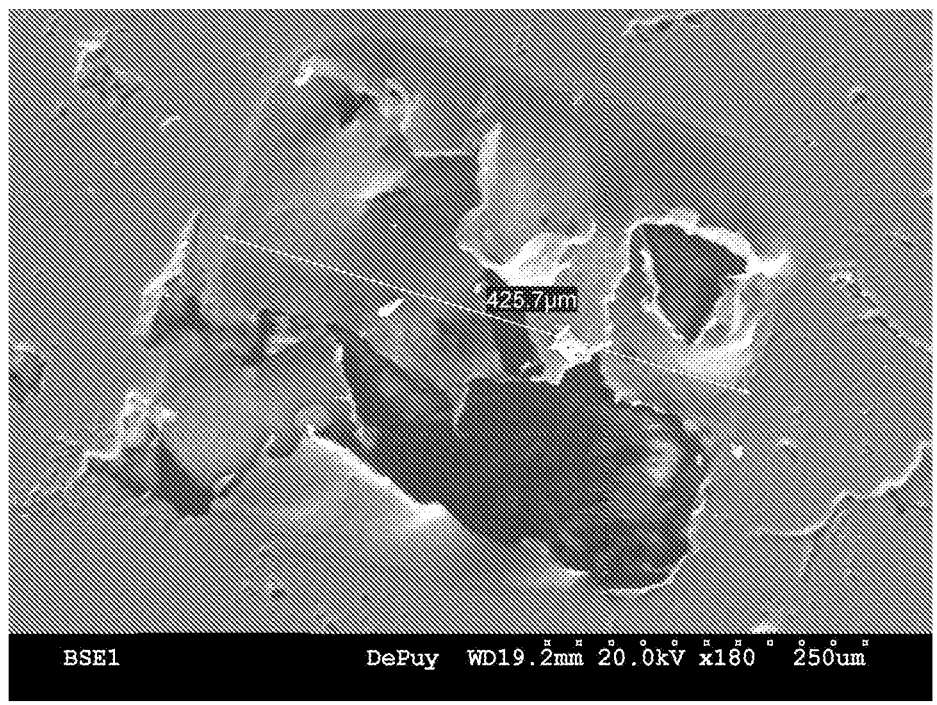
FIG. 4 is an SEM micrograph (180 times magnification) of the surface of porous ultrahigh molecular weight polyethylene (porosity of about 30%) made using the process of the invention. The micrograph also includes measurements of some of the pores present in the porous ultrahigh molecular weight polyethylene.
Figure 5:
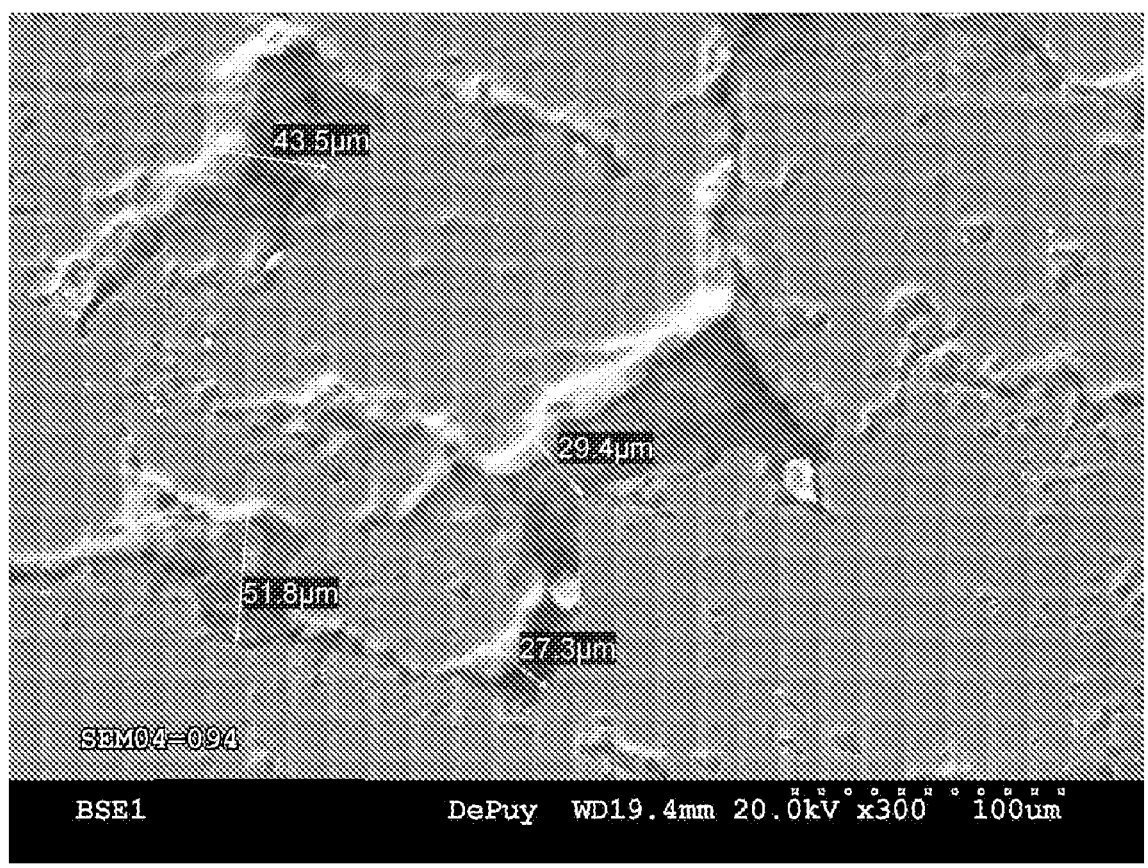
FIG. 5 is an SEM micrograph (300 times magnification) of the surface of porous ultrahigh molecular weight polyethylene (porosity of about 30%) made using the process of the invention. The micrograph also includes measurements of some of the pores present in the porous ultrahigh molecular weight polyethylene.

Sample 3 (invention) was prepared by dry blending GUR 1020 powdered ultrahigh molecular weight polyethylene and a porogen comprising POLYOX™ WSR-303 poly(ethylene oxide) (available from The Dow Chemical Company, Midland, Mich.) and sodium chloride. The polyethylene, poly(ethylene oxide), and sodium chloride were mixed in a volume ratio of approximately 70:5:25, respectively. The resulting mixture was placed in a cylindrical compression mold (approximately 10 cm in diameter) having an internal volume. The mixture was then packed into the mold by subjecting the compression mold to a pressure of approximately 340-690 kPa (50-100 psi) for approximately 1-2 minutes. Following the packing step, the temperature within the compression mold was increased from room temperature to approximately 165° C. (330° F.) at a rate of approximately 6° C./min (11° F./min) while the pressure on the compression mold was increased from 0 kPa to about 3450 kPa (500 psi). Once the temperature within the mold reached 165° C. (330° F.), the temperature was increased from 165° C. (330° F.) to approximately 205° C. (400° F.) at a rate of approximately 2.8° C./min (5° F./min), and the pressure was increased from 3450 kPa (500 psi) to approximately 6900 kPa (1000 psi). The temperature and pressure within the compression mold were then maintained at approximately 205° C. (400° F.) and 6900 kPa (1000 psi) for approximately 15 minutes. Following the compression step, the resulting molded disk was cooled from 205° C. (400° F.) to approximately 38° C. (100° F.) at rate of approximately 5.5° C./min (10° F./min) while the pressure was reduced from 6900 kPa (1000 psi) to approximately 2280 kPa (330 psi). The resulting molded disk was then removed from the compression mold and immersed in water for approximately 168 hours to extract the porogen (i.e., poly(ethylene oxide) and sodium chloride) therefrom. After the extraction step, the resulting sample was dried under vacuum at a temperature of approximately 60° C. for approximately 240 minutes. The resulting sample was measured and weighed to determine its porosity, which was determined to be approximately 30%. The surface of the sample was then analyzed using SEM. SEM micrographs (35×, 180×, and 300× magnification) of the surface of Sample 3 are provided in FIGS. 3-5. The SEM micrographs were further analyzed using the Quartz PCI image acquisition software to determine the diameter of the pores present on the surface of the sample. The pore diameter measurements for selected pores are provided in FIGS. 3-5.

A comparison of the SEM micrographs and pore size measurements for each of the samples reveals that the porous ultrahigh molecular weight polyethylene produced by the process of the invention exhibits a surface morphology and pore size characteristics that are different from porous ultrahigh molecular weight polyethylene having a similar porosity that was produced by a sintering process. In particular, the surfaces of Samples 1 and 2 (comparative) are comprised of a network of roughly round polyethylene particles fused about their outer surfaces to several adjacent polyethylene particles. The interstitial spaces in the network of particles form the pores present in the samples. The pores at the surface of Sample 2 (33% porosity) measured up to approximately 100 μm in diameter. By way of contrast, Sample 3 (invention), which had approximately the same porosity as Sample 2 (comparison), comprised a substantially continuous expanse of ultrahigh molecular weight polyethylene having pores distributed across its surface. The pores in the surface of Sample 3 measured from approximately 25 μm up to approximately 425 μm in diameter. The foregoing results demonstrate that, unlike porous ultrahigh molecular weight polyethylene made by a sintering process, the porous ultrahigh molecular weight polyethylene of the invention comprises a combination of pores having relatively small diameters (e.g., about 100 μm or less) and pores having relatively large diameters (e.g., about 200 to about 400 μm).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A medical implant or medical implant part comprising porous ultrahigh molecular weight polyethylene, wherein (i) the ultrahigh molecular weight polyethylene has a weight average molecular weight of about 400,000 atomic mass units or more, (ii) the ultrahigh molecular weight polyethylene has a porosity of 20% or more, (iii) the average diameter of the pores in the ultrahigh molecular weight polyethylene is about 200 to about 400 μm, and (iv) optionally some of the ultrahigh molecular weight polyethylene comprises hydrophilic functional groups attached thereto.

2. The medical implant or medical implant part of claim 1, wherein the ultrahigh molecular weight polyethylene has a weight average molecular weight of 1,000,000 atomic mass units or more.

3. The medical implant or medical implant part of claim 1, wherein some of the ultrahigh molecular weight polyethylene comprises hydrophilic functional groups attached thereto and the hydrophilic functional groups comprise one or more functional groups selected from the group consisting of amino functional groups, carboxylic acid functional groups, hydroxyl functional groups, and combinations thereof.

4. The medical implant or medical implant part of claim 3, wherein the hydrophilic functional groups comprise one or more carboxylic acid functional groups.

5. The medical implant or medical implant part of claim 1, wherein some of the ultrahigh molecular weight polyethylene comprises hydrophilic functional groups attached thereto and the hydrophilic functional groups are attached to the surface of the ultrahigh molecular weight polyethylene through hydrophilic monomers.

6. A medical implant or medical implant part comprising porous ultrahigh molecular weight polyethylene, wherein (i) the ultrahigh molecular weight polyethylene has a weight average molecular weight of about 400,000 atomic mass units or more, (ii) the ultrahigh molecular weight polyethylene has a porosity of 15% to 65%, and (iii) at least about 5% (by volume) of the pores in the ultrahigh molecular weight polyethylene have a diameter of about 200 μm or more.

7. The medical implant or medical implant part of claim 6, wherein the ultrahigh molecular weight polyethylene has a weight average molecular weight of 1,000,000 atomic mass units or more.

8. The medical implant or medical implant part of claim 6, wherein the ultrahigh molecular weight polyethylene has a porosity of 20% to 60%.

9. The medical implant or medical implant part of claim 6, wherein 5% or more (by number) of the pores in the ultrahigh molecular weight polyethylene have a diameter of 200 μm or more.

10. The medical implant or medical implant part of claim 6, wherein the average diameter of the pores in the ultrahigh molecular weight polyethylene is 400 μm or less.

11. The medical implant or medical implant part of claim 6, wherein at least some of the ultrahigh molecular weight polyethylene comprises hydrophilic functional groups attached thereto.

12. The medical implant or medical implant part of claim 11, wherein the hydrophilic functional groups comprise one or more functional groups selected from the group consisting of amino functional groups, carboxylic acid functional groups, hydroxyl functional groups, and combinations thereof.

13. The medical implant or medical implant part of claim 12, wherein the hydrophilic functional groups comprise one or more carboxylic acid functional groups.

14. The medical implant or medical implant part of claim 11, wherein the hydrophilic functional groups are attached to the ultrahigh molecular weight polyethylene through hydrophilic monomers.

15. The medical implant or medical implant part of claim 14, wherein the hydrophilic monomer is selected from the group consisting of acrylic acid, poly(ethylene glycol), 2-hydroxyethyl methacrylate, and combinations thereof.

* * * * *